United States Patent [19]

Crescentini et al.

[11] Patent Number: 4,767,503
[45] Date of Patent: Aug. 30, 1988

[54] REMOVAL OF LIGHT IMPURITIES FROM CAPROLACTAM BY DISTILLATION WITH WATER

[75] Inventors: Lamberto Crescentini, Chester; Joseph D. DeCaprio, Hopewell; William B. Fisher, Chester; Roy J. Lilley, Jr., Richmond, all of Va.

[73] Assignee: Allied Corporation, Morris Township, Morris County, N.J.

[21] Appl. No.: 527,044

[22] Filed: Aug. 29, 1983

[51] Int. Cl.⁴ .......................... B01D 3/14; B01D 3/38
[52] U.S. Cl. ........................................ 203/48; 203/92; 203/96; 540/540
[58] Field of Search ................. 203/48, 92, 95, 96, 203/14, 88; 540/540; 23/295; 260/707

[56] References Cited

U.S. PATENT DOCUMENTS

| | | |
|---|---|---|
| 3,600,381 | 8/1971 | Yamamoto et al. ............... 540/540 |
| 3,839,324 | 10/1974 | Schultze et al. .................. 540/540 |
| 3,944,543 | 3/1976 | Goettsch et al. .................. 540/540 |
| 4,148,792 | 4/1979 | Danziger et al. .................. 540/540 |
| 4,148,793 | 4/1979 | Danziger et al. .................. 540/540 |
| 4,311,642 | 1/1982 | Crescentini et al. .............. 540/540 |
| 4,457,807 | 7/1984 | Rulkens et al. ................... 540/540 |

FOREIGN PATENT DOCUMENTS

| | | |
|---|---|---|
| 1445549 | 12/1968 | Fed. Rep. of Germany ...... 540/540 |
| 7024782 | 10/1967 | Japan ................................. 540/540 |
| 0332088 | 5/1969 | U.S.S.R. ............................ 540/540 |

OTHER PUBLICATIONS

Weissberger, "Technique of Organic Chemistry," vol. IV, Distillation, N.Y., 1965, pp. 3 & 9.
Kirk-Othmer, "Encyclopedia of Chemical Technology", 3rd ed., vol. 18, 1807-1982, pp. 425-436.
Oldershaw, "Perforted Plate Column for Analytical Batch Distillation", vol. 13, pp. 265-268, Apr. 1941.

Primary Examiner—David L. Lacey
Assistant Examiner—V. Manoharan
Attorney, Agent, or Firm—Richard A. Anderson

[57] ABSTRACT

This invention is a method of purifying crude caprolactam. The improved method comprises taking a portion of a process stream of crude caprolactam having low boiling impurities and distilling the stream in the presence of water by fractional distillation into an overhead containing water and low boiling impurities and bottoms of caprolactam having improved purity and low water content.

The improvement also comprises taking a low water content stream of crude caprolactam having low boiling impurities and adding water to the stream and distilling the stream by fractional distillation as described above.

7 Claims, 1 Drawing Sheet

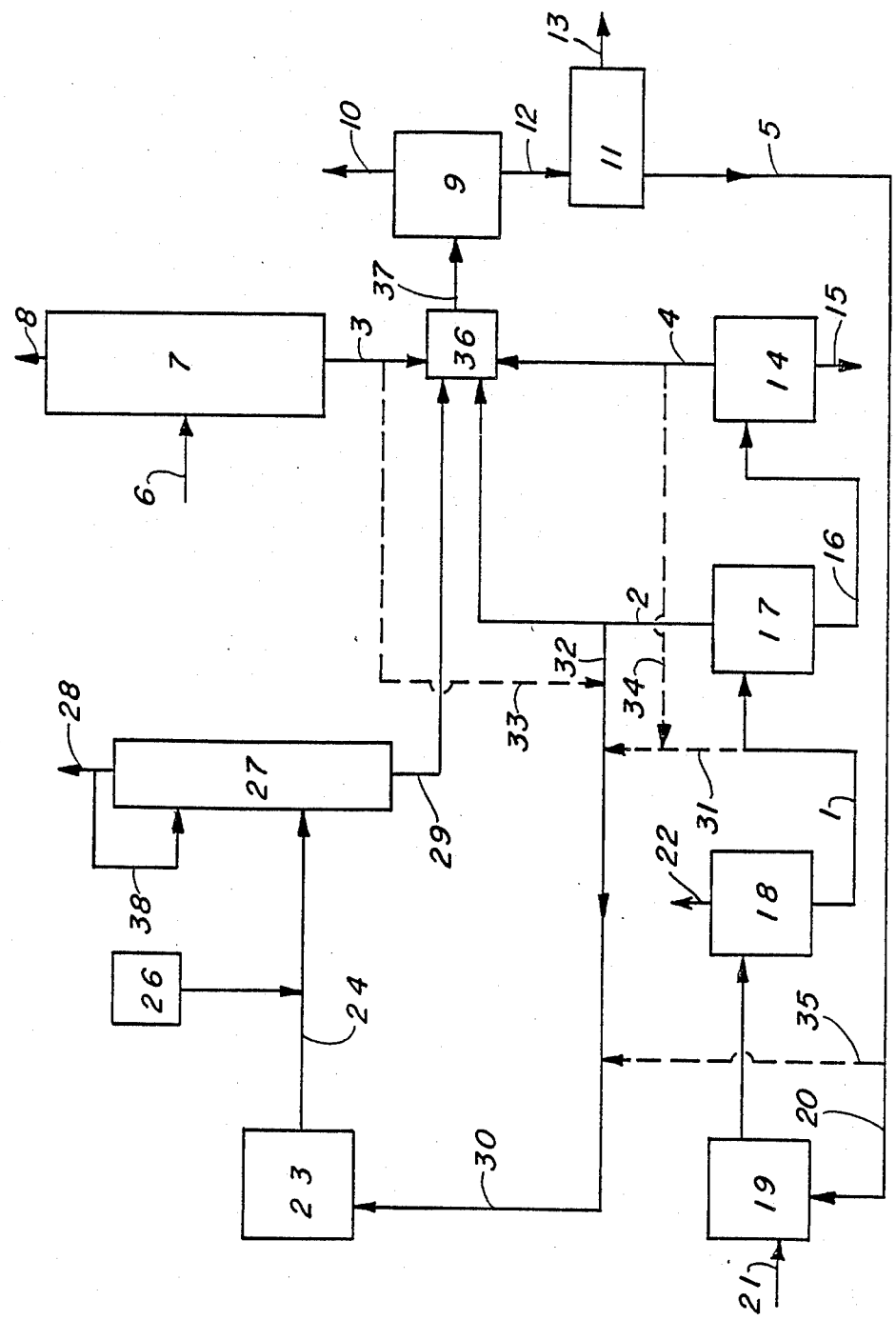

REMOVAL OF LIGHT IMPURITIES FROM CAPROLACTAM BY DISTILLATION WITH WATER

BACKGROUND OF THE INVENTION

This invention relates to the method of removal of light impurities from caprolactam by distillation with water. The crude caprolactam (epsilon-caprolactam) is obtained from the Beckmann rearrangement of cyclohexanone oxime and must be purified for suitable use as a monomer to prepare polycaprolactam (nylon 6). See pages 425-436, Kirk-Othmer: Encyclopedia of Chemical Technology, Vol. 18, 3d Ed. 1982 (John Wiley) hereby incorporated by reference.

The following are definitions of the terms used in this patent application. By portion is meant 2-98%, preferably 5-90% of a process stream. By low boiling is meant those impurities boiling between the atmospheric boiling point of caprolactam and water. By low water content is meant a content below 10% by weight of water. By crude caprolactam is meant caprolactam with impurities from the process and includes mother liquor from the crystallizer of the caprolactam process. The process used for the invention may be batch or continuous. The crystallization used in the process herein can be single or multistage. Also the distillation used in the process herein can be single or multistage.

Many methods to purify crude caprolactam and other lactams are known. See column 1 of U.S. Pat. No. 3,347,852 hereby incorporated by reference. For a water crystallization process, fractional crystallization or solvent extraction may be used in the crude caprolactam or mother liquor as in U.S. Pat. No. 2,817,661 or U.S. Pat. No. 3,761,467, both hereby incorporated by reference. Multistage centrifuges and freezer crystallizers may be used as in U.S. Pat. No. 2,813,858, hereby incorporated by reference. Crystallization may be used from special solvents as in U.S. Pat. No. 3,966,712, hereby incorporated by reference. Also, solvent may be removed from crystallized lactam by distilling in the presence of water as in U.S. Pat. No. 4,148,793, hereby incorporated by reference.

SUMMARY OF THE INVENTION

This invention is a method to purify crude caprolactam. The improvement consists essentially of taking a portion of the process stream of crude caprolactam having low boiling impurities and distilling the stream in the presence of water by fractional distillation into an overhead containing water and low boiling impurities and bottoms of caprolactam having improved purity and low water content.

This invention, in a second embodiment, is also a method to purify crude caprolactam wherein the improvement comprises taking a low water content stream of crude caprolactam having low boiling impurities, adding water to the stream, distilling the stream by fractional distillation into an overhead containing water and low boiling impurities and bottoms of caprolactam with improved impurities and low water content. The bottoms of the fractional distillation step is recovered and fed to a crystallizer to form crystals of caprolactam. Also, in a preferred second embodiment, only a portion of the stream would be taken from the process to be fed to the first step. Preferably, this stream fed to the first step of the process contains about 0.1% to about 10% by weight of water. Even more preferably, the stream fed to the process of the first step contains about 0.5% to about 3% by weight of water, water is added in the second stage from a ratio from about 0.15 to 1 to about 0.5 to 1 by the weight of the stream of the first step, the distillation of the stream removes from about 4% to about 45% of all impurities as measured by permanganate number, the reflux ratio during said distillation step is between about 0.25 to 1 to about 5 to 1, the caprolactam content of the overheads from the distillation step is below about 3% by weight, and the water content of the bottoms from distillation step is between about 0.1% to 5% by weight.

BRIEF DESCRIPTION OF THE DRAWING

The FIGURE is a schematic showing preferred embodiments of the invention.

DESCRIPTION OF THE PREFERRED EMBODIMENTS

The drawing shows the preferred embodiment having ten vessels; the distillation column 7, crystallizer 9, filter 11, thin-film evaporator 14, flasher 17, flasher 18, tank 19, tank 23, tank 36, and distillation column 27. Crude lactam (caprolactam) from the Beckmann rearrangement process, containing water and impurities is fed through line 6 to distillation column 7 where water is distilled overhead through line 8 and lactam and water are fed through line 3 to feed tank 36 through line 37 to crystallizer 9 where water is again taken overhead through line 10 and wet caprolactam crystals are fed through line 12 to filter 11 and the pure caprolactam crystals are removed through line 13 and mother liquor is removed through line 5 to tank 19 where other various impure caprolactam streams are added through line 21. Tank 19 feeds flasher 18 through line 20. Water and caprolactam are removed overhead from flasher 18 in line 22 and caprolactam-rich bottoms are fed through line 1 to caprolactam flasher 17 where caprolactam is flashed overhead through line 2 and bottoms are fed through line 16 to thin-film evaporator 14 which flashes overheads to line 4 and heavy residues are removed through line 15 to recovery or disposal. Overhead lines 2 and 4 are also fed to feed tank 36 and line 37 to crystallizer 9 where water is removed and caprolactam crystals are sent to filter 11 as described above. The process described above is known in the prior art. The improvement is described as follows. All or portions of the streams or flows in lines 1, 2, 3, 4 and/or 5 can be diverted through lines 33, 35, 34, 31, and/or 32 to line 30 which feeds into feed tank 23. The schematic shows the preferred stream 2 being fed through line 32 and feed lines 31, 33, 34 and 35 as alternates or additional streams. Feed tank 23 feeds distillation column 27 through line 24. If feed tank 23 is low in water content, water from source 26 is fed through line 25 into line 24. Water and low boiling impurities are removed overhead from column 27 through line 28, and bottoms containing purified lactam of low water content is sent through line 29 to feed tank 36 through line 37 to crystallizer 9 to be processed as above-described. Reflux to column 27 is through line 38.

EXAMPLES

When crude caprolactam is purified by crystallization from aqueous solution, purified crystals are separated from an aqueous mother liquor containing impurities and considerable amounts of lactam. It is not economical to discard the mother liquor without first recovering most of the lactam in it. Lactam is usually recovered by flash distillation, and it is recycled to crystallization. We have found in a preferred embodiment of this invention that if water is added to the flashed lactam (in the drawing stream Number 2) and this material is subjected to a new, fractional distillation step, after water addition, a large proportion of the impurities can be eliminated as a light aqueous fraction with negligible loss of lactam, leaving a bottoms product for recycle substantially purer than the feed.

Streams from a commercial operation representing stages in the lactam flashing and recycle process and the feed stream to crystallization itself behaved similarly in laboratory distillations, i.e., substantial amounts of impurities could be removd by fractional steam distillation as light fractions. Impurities were measured as permanganate number (PN) (method described in U.S. Pat. No. 3,406,167 and U.S. Pat. No. 3,021,326, both hereby incorporated by reference). Quantitative data are shown in the table as percent PN removed. Water added is shown as percent of feed. Best representative examples include 23-7, 23-12, 23-26 and 23-28. Benefits from removal of these light boiling impurities from the recycled stream are a crystallized product lactam of better quality and increased crystallization capacity for the same product lactam quality. (Overall PN value). Impurities not removed in this way would leave the system as contaminants in the product.

Plant streams tested in this work have the following approximate composition:

TABLE I

| Stream | % Lactam | % Water | Permanganate No. |
|---|---|---|---|
| 1. Bottoms | 99 | 1 | 2000 |
| 2. Overheads | 98 | 2 | 2000 |
| 3. Bottoms | 92 | 8 | 500 |
| 4. Overheads | 99+ | <1 | 1500 |
| 5. Mother Liquor | 93 | 7 | 2000 |

The above numbers, 1 to 5, indicate the same numbered streams as those in the drawing.

TYPICAL EXPERIMENT

A one-inch (inside diameter) Oldershaw column containing fifteen perforated plates (number of plates can be varied), equipped with a reflux condenser, overhead sample take-off, and a reboiler in bottom of column was used for all experiments.

The Oldershaw column consists of a series of perforated glass plates sealed in a glass tube. Each plate is equipped with a baffle to direct the flow of liquid, a weir to maintain a liquid level on the plates, and a drain pipe. The first plate in a series serves as a small reservoir which is necessary in order to maintain a liquid seal for the drain pipe from the first regular plate. Further description is found in C. F. Oldershaw, Perforated Plate Column, Industrial & Engineering Chemistry, Vol. 13, No. 4, pages 265–268 (April, 1941), hereby incorporated by reference.

Stream 2, the overhead from lactam flasher, is the preferred stream for use in the removal of light impurities as measured by permanganate number.

The feed material containing the water was fed into the side of the column above the fifth plate; although other feed ports were evaluated, the addition at the fifth plate gave best results. Table II shows the parameters and results of many experimental runs on the Oldershaw column. All experiments were carried out under 10 mm Hg pressure. The ratio of light impurities (PN's) to total impurities is highest in stream No. 2. In run of Experiment No. 14-45, no external reflux was used, only internal reflux was occurring. For runs using stream No. 5 as feed, no water was added. For Experiment No. 29-4, an uneven run occurred due to feed pump pluggage.

TABLE II

CONTINUOUS DISTILLATIONS

| Expt. No. | $H_2O$ Added as % of Feed | Total $H_2O$ as % of Feed | Overhead as % of Feed | % PN Removed | % Lactam Lost | Reflux Ratio | Feed Rate, cc/Minute | Stream Number Used as Feed |
|---|---|---|---|---|---|---|---|---|
| 23-7  | 33 | 34.3 | 33 | 45 | 2.7   | 3:1 | 1.5 | 2 |
| 23-11 | 33 | 34.3 | 33 | 29 | 0.08  | 3:1 | 1.5 | 2 |
| 23-12 | 33 | 34.3 | 33 | 27 | 0.03  | 3:1 | 1.5 | 2 |
| 23-1  | 33 | 34.3 | 31 | 24 | Neg.  | 1:1 | 1.5 | 2 |
| 23-14 | 33 | 34.3 | 21 | 19 | Neg.  | 2:1 | 1.5 | 2 |
| 14-50 | 33 | 34.3 | 30 | 17 | 0.005 | 1:1 | 2.0 | 2 |
| 23-3  | 33 | 34.3 | 25 | 19 | Neg.  | 2:1 | 1.5 | 2 |
| 23-13 | 33 | 34.3 | 25 | 14 | Neg.  | 3:1 | 1.5 | 2 |
| 14-49 | 33 | 34.3 | 24 | 13 | Neg.  | 1:1 | 2.0 | 2 |
| 14-45 | 33 | 34.3 | 19 | 5  | Neg.  | *   | 3.0 | 2 |
| 23-24 | 25 | 26.5 | 25 | 23 | Neg.  | 3:1 | 1.5 | 2 |
| 23-26 | 15 | 16.7 | 16 | 28 | 0.008 | 3:1 | 1.5 | 2 |
| 23-28 | 15 | 16.7 | 15 | 27 | Neg.  | 3:1 | 3.5 | 2 |
| 23-29 | 15 | 16.7 | 17 | 25 | Neg.  | 2:1 | 2.5 | 2 |
| 23-31 | 15 | 16.7 | 16 | 24 | 0.02  | 1:1 | 3.5 | 2 |
| 29-2  | 25 | 25.75 | 25 | 18 | Neg.  | 3:1 | 2.0 | 1 |
| 29-6  | 25 | 25.75 | 27 | 18 | 0.8   | 2:1 | 2.0 | 1 |
| 29-4  | 25 | 25.75 | 25 | 13 | 0.4   | 2:1 | 2.0 | 1 |
| 23-50 | 15 | 15.8 | 14 | 12 | Neg.  | 3:1 | 3.5 | 1 |
| 23-46 | 15 | 15.8 | 17 | 10 | 0.02  | 1:1 | 2.5 | 1 |
| 23-47 | 15 | 15.8 | 15 | 5  | 0.06  | 2:1 | 3.0 | 1 |
| 29-7  | 24 | 30   | 26 | 19 | 0.7   | 2:1 | 2.0 | 3 |
| 29-9  | 25 | 25   | 26 | 20 | 0.2   | 2:1 | 2.0 | 4 |
| 29-11 | 25 | 25   | 20 | 9  | 0.01  | 3:1 | 1.5 | 4 |
| 23-45 | —  | 7    | 7  | 20 | Neg.  | 1:1 | 5.0 | 5 |
| 23-32 | —  | 7    | 10 | 16 | Neg.  | 1:1 | 5.0 | 5 |

TABLE II-continued

CONTINUOUS DISTILLATIONS

| Expt. No. | H₂O Added as % of Feed | Total H₂O as % of Feed | Overhead as % of Feed | % PN Removed | % Lactam Lost | Reflux Ratio | Feed Rate, cc/Minute | Stream Number Used as Feed |
|---|---|---|---|---|---|---|---|---|
| 23-41 | — | 7 | 7 | 9 | Neg. | 2:1 | 5.0 | 5 |
| 23-40 | — | 7 | 5 | 4 | Neg. | 1:1 | 5.0 | 5 |
| 23-43 | — | 7 | 6 | 4 | Neg. | 3:1 | 5.0 | 5 |

*Indicates internal reflux only.

We claim:
1. In a method to purify crude caprolactam, the improvement consisting essentially of
   (a) taking a water content below 10% stream of crude caprolactam having impurities,
   (b) adding water to said stream, and
   (c) distilling said stream by fractional distillation into an overhead containing water and low boiling impurities and a bottoms of caprolactam with water content below 10%.
2. The method of claim 1 wherein the bottoms of step (c) is fed to a crystallizer to form crystals of caprolactam.
3. The method of claim 1 wherein the stream of step (a) contains between about 0.1% and about 10% by weight water.
4. The method of claim 2 wherein the stream of step (a) contains between about 0.5% and about 3% by weight water, water is added in step (b) at a ratio of from about 0.15 to 1 to about 0.5 to 1 by weight of stream of step (a), the distillation of step (c) removes from about 4% to about 45% of the impurities as measured by permanganate number, the reflux ratio during said distillation of step (c) is between about 0.25 to 1 and about 5 to 1, the caprolactam content of the overheads from the distillation of step (c) is below about 3% by weight, and the water content of the bottoms from distillation step (c) is between about 0.1% and 5% by weight.
5. The method of claim 1 wherein water added in step (b) achieves at least 15.8% by weight water in said stream of step (b).
6. In a method to purify crude caprolactam the improvement consisting essentially of
   a. taking a portion of a water content below 10% stream of caprolactam having low boiling impurities,
   b. adding water to said stream, and
   c. distilling said stream by fractional distillation into an overhead containing water and low boiling impurities and bottoms of caprolactam with water content below 10%.
7. The method of claim 5 wherein water added in step (b) achieves at least 15.8% by weight water in said stream of step (b).

* * * * *